United States Patent [19]

Vértesy et al.

[11] Patent Number: 5,091,524
[45] Date of Patent: Feb. 25, 1992

[54] GLYCOSIDASE INHIBITOR SALBOSTATIN, PROCESS FOR ITS PREPARATION, AND ITS USE

[75] Inventors: László Vértesy, Eppstein/Taunus; Hans-Wolfram Fehlhaber, Idstein/Taunus; Arno Schulz, Hattersheim am Main, all of Fed. Rep. of Germany

[73] Assignee: Hoechst Aktiengesellschaft, Frankfurt, Fed. Rep. of Germany

[21] Appl. No.: 426,805

[22] Filed: Oct. 26, 1989

[30] Foreign Application Priority Data

Oct. 28, 1988 [DE] Fed. Rep. of Germany ....... 3836675

[51] Int. Cl.$^5$ ................ C07D 309/14; A61K 31/35; C12P 13/00; A01N 43/16
[52] U.S. Cl. ..................... 536/18.7; 536/22; 47/58; 435/72; 435/84; 435/85; 435/169; 435/293.5; 435/887; 514/23; 514/866; 514/884; 514/909
[58] Field of Search ................. 536/22, 18.7; 435/72, 435/84, 85, 253.5, 169, 887; 47/58; 514/23, 866, 884, 909

[56] References Cited

U.S. PATENT DOCUMENTS

| | | |
|---|---|---|
| 4,062,950 | 12/1977 | Frommer et al. ............... 536/17 |
| 4,065,557 | 12/1977 | Frommer et al. ............... 536/18 |
| 4,254,256 | 3/1981 | Otani et al. .................... 536/18 |
| 4,762,833 | 8/1988 | Kreutzberger et al. ......... 514/245 |
| 4,864,027 | 9/1989 | Shubert et al. ................. 546/14 |

FOREIGN PATENT DOCUMENTS 0224024 6/1987 European Pat. Off. .
0240853 10/1987 European Pat. Off. .

OTHER PUBLICATIONS

Truscheit et al., Angew. Chem. 93 (1981), pp. 738–755.

Primary Examiner—Ronald W. Griffin
Attorney, Agent, or Firm—Finnegan, Henderson, Farabow, Garrett and Dunner

[57] ABSTRACT

Salbostatin, a compound of the formula I acts as a glycosidase inhibitor and is suitable for use in pharmacy and in plant protection.

9 Claims, 1 Drawing Sheet

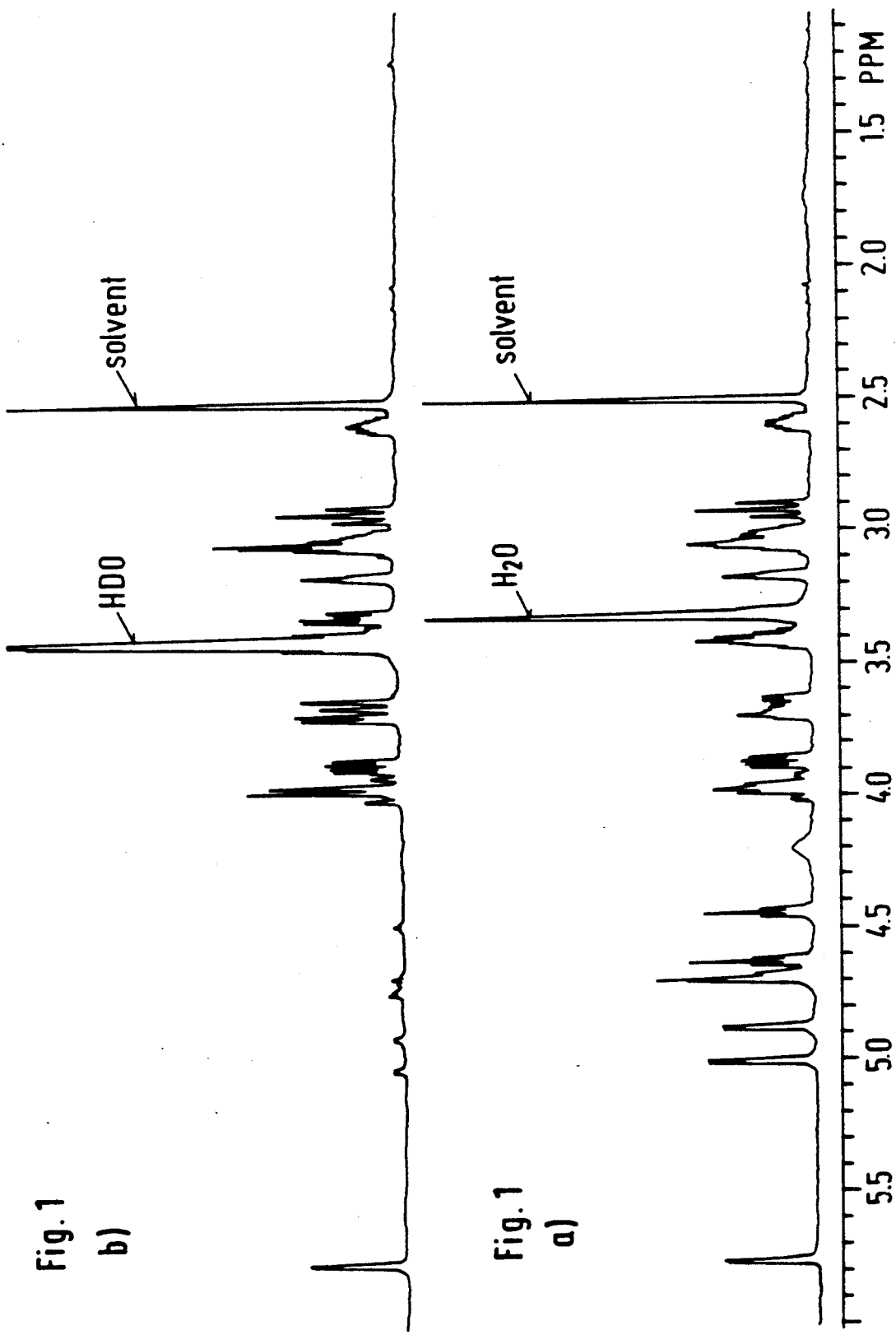

GLYCOSIDASE INHIBITOR SALBOSTATIN, PROCESS FOR ITS PREPARATION, AND ITS USE

The present invention relates to the biologically active pseudodisaccharide salbostatin, to its physiologically acceptable salts, to a process for its preparation, and to its use in pharmacy and in plant protection.

Salbostatin is a basic, non-reducing pseudodisaccharide which has the formula I and characteristic chemical or physical properties.

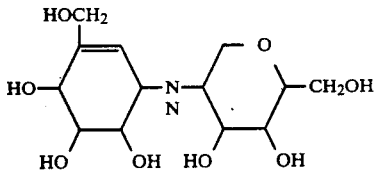

Basic pseudodisaccharides having an enzyme-inhibiting action have repeatedly been described in the literature (see U.S. Pat. Nos. 4,062,950, 4,065,557 and 4,254,256, and also E. Truscheit et al. Angew. Chem. 93, 738–755, (1981)). They have saccharose-inhibiting and maltose-inhibiting or antimicrobial properties and can be employed, for example, in the treatment of diabetes mellitus or as antibiotics.

Salbostatin, the substance according to the invention, has a glycosidase-inhibiting activity and is therefore suitable for application in pharmacy and in plant protection.

Salbostatin has the following configuration:

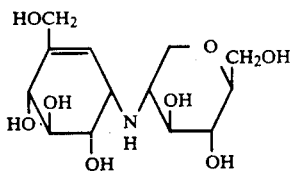

Such a basic, cyclic, non-reducing ether has not yet been described.

Another subject of the invention are obvious chemical equivalents and physiologically acceptable salts of salbostatin, in particular acid addition salts, such as, for example, the hydrochloride, which can be prepared in a generally known manner.

The invention furthermore relates to a process for the preparation of salbostatin in which (a) the commercially available microorganism Streptomyces albus (ATCC 21838) and its variants and mutants are grown in a culture medium until the compound of the formula I is accumulated in the culture, and, if appropriate, the compound is (b) isolated and purified and derivatives are formed.

Salbostatin, inter alia, is produced by Streptomyces albus ATCC 21838 in a nutrient solution which contains a carbon source and a nitrogen source and the inorganic salts which are customary for these purposes.

It is of course possible to use the mutants and/or variants in place of strain ATCC 21838 if they synthesise the compound according to the invention. Such mutants can be produced in a manner known per se by ultraviolet radiation or x-rays, or by chemical mutagens, such as, for example, methyl ethanesulfonate (EMS) or 2-hydroxy-4-methoxybenzophenone (MOB).

Examples of preferred carbon sources for the aerobic fermentation are metabolizable carbohydrates and sugar alcohols, such as glucose, lactose or D-mannitol and carbohydrate-containing natural products, such as malt extract, and also oils and fats. Possible nitrogen-containing nutrients are, inter alia, amino acids, peptides and proteins and their degradation products, such as peptones or tryptones, furthermore meat extracts, ground seeds, for example seeds of maize, wheat, beans, soya beans or of the cotton plant, distillation residues from alcohol production, meat meals or yeast extracts, but also ammonium salts and nitrates. Examples of other inorganic salts which the nutrient solution can contain are chlorides, carbonates, sulfates or phosphates of the alkali metals or alkaline earth metals, or trace elements, such as, for example, iron, zinc, cobalt and manganese.

Salbostatin is particularly advantageously formed in a nutrient solution which contains 0.1 to 15% of nutrient constituents, such as soya bean meal, soya bean oil and manitol, in particular 0.1 to 3% in each case, relative to the weight of the total nutrient solution. The fermentation is preferably aerobic, for example submerse, with shaking or stirring in shaken flasks or fermenters, if appropriate with air or oxygen passed in. The fermentation can be carried out within a temperature range of about 18° to 35° C., preferably at about 25° to 30° C., in particular 28° to 30° C. The pH range should be between 6 and 8, advantageously between 6.5 and 7.5. Under these conditions, the culture mixture usually shows an appreciable concentration of salbostatin after 6 to 15 days.

It is advantageous to culture the fungus in several steps, i.e., one or more precultures are first established in a liquid culture medium, and the actual production medium, the main culture, is then inoculated with these, for example in a ratio of 1:10 by volume. The preculture is obtained, for example, by inoculating a nutrient solution with a spore-producing mycelium and allowing the culture to grow for about 80 to 400 hours. The spore-producing mycelium can be obtained by growing the strain for about 12 days on a solid or liquid culture medium, for example yeast-malt agar.

The process of the fermentation can be monitored by means of the pH of the culture or the volume of the mycelium, or by an assay of the biological activity. Both the mycelium and the culture filtrate contain salbostatin. However, the bulk of salbostatin is generally found in the culture filtrate.

The compounds mentioned are isolated from the culture medium by known methods taking into account the chemical, physical and biological properties of the products, such as, for example, by chromatography on ion-exchangers, molecular sieves, adsorption resins and reversed-phase supports, and by precipitation in solvents, reverse osmosis and others.

It is furthermore advantageous to separate the aqueous phase from the mycelium, for example by filtration or centrifugation, and to isolate and then purify the salbostatin from the respective phases.

A preferred method comprises extracting the culture filtrate with butanol to remove the fats, and concentrating the aqueous phase in vacuo. The aqueous concentrate which is diluted with the 2- to 5-fold amount of methanol is freed by centrifugation from the high-molecular-substances which have precipitated. In the next step, the basic constituents are isolated from the aqueous-methanolic supernatant using strongly acid ion exchangers, such as, for example, ®Dowex 50 WX 2.

The amphoteric substances are then removed from this using an anion exchanger, such as, for example, ®Amberlite IRA-68. The basic fraction which remains contains the salbostatin. After demineralization with the aid of a molecular sieve, such as, for example, ®Sephadex LH-2, the pure salbostatin is obtained by separation by means of ion-exchanger chromatography and renewed demineralization. FIG. 1 shows $^1$H-NMR spectra of the pure salbostatin. Spectrum a) was recorded in $d_6$-DMSO at 400 MHz and 300 K; the chemical shift relates to TMS Spectrum b) was recorded in $d_6$-DMSO with the addition of 1% of HzO at 300 K.

Salbostatin, according to the invention, is suitable as a glycosidase inhibitor for therapy of metabolic diseases in humans and in homothermal animals. As a trehalase inhibitor, salbostatin is suitable as a plant protection agent. Trehalose is an important energy-storing substance for insects, fungi and also in the plant kingdom, for example in some pollen grains. Trehalose metabolism, which is of virtually no importance for homothermals, always includes the hydrolytic enzyme trehalase. If this enzyme is inhibited, it is possible to target selectively those organisms which are trehalase-dependent.

Inhibition of the enzyme trehalase by salbostatin is highly effective. $10^{-7}$ to $10^{-8}$ molar salbostatin solutions already show an enzyme inhibition of 50%. More detailed investigations into enzyme kinetics showed that salbostatin is a competitive trehalase inhibitor with regard to trehalose. The inhibitor constant Ki is $1.8 \times 10^{-7}$ M.

The present invention furthermore relates to pharmaceutical preparations and to plant protection agents which show a content of a compound according to the invention and which can be prepared by generally known methods (cf., for example, European Patents 0,240,853 and 0,224,024 which correspond, respectively, to U.S. Pat. Nos. 4,864,027 and 4,762,833).

As taught in U.S. Pat. No. 4,864,027, the invention also relates to agents which contain the compounds of the formula I in addition to suitable formulation auxiliaries. They can be used in the conventional preparations as wettable powders, emulsifiable concentrates, sprayable solutions, dusting agents or granulates.

Wettable powders are preparations which can be dispersed uniformly in water and which also contain, besides the active compound and a diluent or inert substance, wetting agents and dispersing agents.

Emulsifiable concentrates are prepared by dissolving the active compound in an organic solvent with addition of one or more emulsifiers.

Dusting agents are obtained by grinding the active compound with finely divided solid substances, for example talc or natural clays. Granules can be prepared either by atomizing the active compound onto absorptive, granulated inert material or by applying the active compound concentrates by means of adhesives onto the surface of carrier materials such as sand, kaolinites or granulated inert material. Suitable active compounds can also be prepared in the conventional fashion for the preparation of fertilizer granulates.

Similarly, it is taught in U.S. Pat. No. 4,762,833 that the medicaments according to the invention contain the compound of the formula I as active compound, where appropriate in combination with other active compounds.

The medicaments are prepared by methods known per se and familiar to the expert. The medicament is used in the form of tablets, coated tablets, capsules, suppositories, emulsions, suspensions or solutions with an effective amount of the said active compound either per se or, preferably, in combination with suitable pharmaceutical auxiliaries. The auxiliaries suitable for the desired medicament formulation are familiar to the expert on the basis of his expert knowledge. In addition to tableting auxiliaries, solvents, gel-forming agents, suppository bases and other vehicles for active compounds it is possible to use, for example, antioxidants, dispersants, emulsifiers, antifoam agents, flavorings, preservatives, solubilizers or colorants.

The active compound can be administered orally, parenterally, intravenously or rectally, with oral administration being preferred. For a form for oral use, the said active compound is mixed, where appropriate with further active compounds, with the additives suitable for this purpose, such as excipients, stabilizers or inert diluents, and converted by the customary methods into suitable presentations such as tablets, coated tablets, hard gelatin capsules and aqueous, alcoholic or oily suspensions or solutions.

For subcutaneous or intravenous administration, the active compound is converted into a solution, suspension or emulsion, if desired with the substances customary for this purpose, such as solubilizers, emulsifiers or other auxiliaries.

Trehalase Assay

The trehalase assay is based on the colorimetric determination of D-glucose, which is liberated from trehalose by the action of trehalase.

Before the assay was started, trehalase (Sigma No. T 8778) was diluted with 20 mM phosphate buffer pH 6.5 in a ratio of 1 1000. Trehalose was dissolved in a concentration of 0.1M in 0.1M 2-(n-morpholino)ethanesulfonic acid.

At the beginning of the assay, 100 μl each of $H_2O$, trehalose and trehalase were combined and the mixture was incubated at 37° C. for 30 minutes. The reaction was stopped by heating the batch to 100° C. The control batch was stopped immediately (0 minutes) by boiling. Where appropriate, salbostatin was added to the reaction batches in various concentrations in place of water.

The glucose which was liberated from the trehalose was determined colorimetrically. To this end, the glucose was reacted by glucose oxidase and the $H_2O_2$ which formed was used for oxidizing o-dianisidine. The oxidized odianisidine was determined using a photometer. All the abovementioned reagents for glucose determination came from the glucose kit manufactured by Sigma (Sigma Chemie GmbH, Deisenhofen, Germany; No. 510-DA), and the assay was carried out in accordance with the enclosed protocol.

EXAMPLE 1

Obtaining Salbostatin by Fermentation (2000 1)

To obtain the glucosidase inhibitor according to the invention by fermentation, the producing microorganism Streptomyces albus ATCC 21838 was cultured starting from a freeze-dried permanent form of this strain, as is customary in microbiology. The fungus was first cultured on the solid culture medium in sterile Petri dishes. Individual colonies were then cultured further in slanted agar tubes, and the mass production of spores, which is necessary for fermentation, was carried out in Roux bottles using these cultures.

Agar medium for passages on solid culture media:

| | |
|---|---|
| Dextrin | 15.0 g/l |
| Sucrose | 2.0 g/l |
| Meat extract | 1.0 g/l |
| Yeast extract | 2.0 g/l |
| Sodium chloride | 0.5 g/l |
| $K_2HPO_4$ | 0.5 g/l |
| $FeSO_4.7H_2O$ | 0.01 g/l |
| Agar-agar | 2.0 g/l |
| pH | 7.3 |
| Sterilization at 120° C., for 20 minutes | |
| Incubation at 30° C., for 9 days | |

The spore suspension of one Roux bottle was taken up in 100 ml of sterile water and used as the inoculum for the first preliminary stage of submerse vegetative fermentation (batch volume 1.2 l).

Medium for the preliminary stage:

| | |
|---|---|
| Soluble starch | 4.0 g/l |
| Glucose | 1.0 g/l |
| Casein peptone | 1.0 g/l |
| Corn-steep liquor | 0.4 g/l |
| Soya bean meal | 0.4 g/l |
| $(NH_4)_2SO_4$ | 0.8 g/l |
| pH | 8.3 |
| Sterilization at 120° C., for 20 minutes | |
| Incubation at 18° C., for 2 days, on a shaker at 150 ipm and 5 cm amplitude | |

After 48 hours, the contents of one Fernbach flask with the resulting first preculture (see above) were used as the inoculum for the second preliminary stage, 200 l in volume, again with the medium for the preliminary stage (see above) being used. The sterilization time was 30 minutes. Incubation was carried out for over 48 hours at 28° C. with stirring at a peripheral speed of 5 m/sec and at an aeration rate of 0.1 vvm.

The contents of the second preculture were used as the inocumum for the main fermentation.

Medium for main fermentation:

| | |
|---|---|
| Peanut meal | 30.0 g/l |
| Corn-steep solids | 10.0 g/l |
| Maize starch | 20.0 g/l |
| Dextrin | 40.0 g/l |
| $(NH_4)_2SO_4$ | 5.0 g/l |
| $MgSO_4.7H_2O$ | 5.0 g/l |
| $CaCO_3$ | 8.0 g/l |
| pH | 6.8 |
| Sterilization at 120° C., for 50 minutes | |

The main fermentation was carried out at 28° C. with stirring, at a peripheral speed of 4 m/sec and at an aeration rate of 0.6 vvm. The formation of the inhibitors according to the invention started after 4 days and reached a maximum after 10 to 12 days. After the fermentation maximum had been reached, the contents of the fermenter were harvested. The yield of salbostatin, of the formula I, was between 0.5 and 5 mg/l of culture solution.

EXAMPLE 2

Isolation of Salbostatin from the Culture Solution 2000 l of fermentation solution from Example 1 were freed from the biomass with the aid of a filter press, and the clear liquid was extracted twice using 600 l of n-butanol each time. The fat was removed from the aqueous phase, the latter was then concentrated in vacuo in a down-draft evaporator at 150 l, and this concentrate was then diluted using 600 l of methanol. This resulted in the formation of a pale, flocculate precipitate which was separated by centrifugation and discarded. The aqueous-methanolic supernatant was again concentrated in vacuo and dried to give 18 kg of a brown, sticky product. This was then adsorbed in an aqueous medium on 70 l of cation exchanger ®;Dowex 50 WX 2 (acid form), the loaded exchanger was washed with clean water, and the inhibitors were desorbed using 0.5 M ammonium hydroxide solution. The trehalase-inhibiting eluates were collected and freeze-dried (3.5 kg). The amorphous compounds were separated from this by an analogous procedure on 70 l of anion exchanger ®Amberlite IRA-68. The eluate from the column contained the salbostatin. Freeze-drying of the inhibitory-active eluate gave 850 g of dry product. Gelchromatography on Sephadex LH-20 and freeze-drying of the active material gave 62 g of crude salbostatin.

30 g of this material were then applied to an S-Sepharose Fast Flow column of content 2.4 l. The cation exchanger had previously been equilibrated with ammonium acetate buffer, pH 3.1.

Salbostatin was eluted using a 0 to 0.6 molar ammonium acetate gradient. The trehalase-inhibiting fractions were freeze-dried and then demineralized on Sephadex LH-20 and again on Fractogel TSK HW-40, followed by freeze-drying. The result was 520 mg of pure, amorphous, white salbostatin. The optical rotation $[\alpha]_D$ is +115° (c=1 in water).

We claim:

1. A compound of the formula I

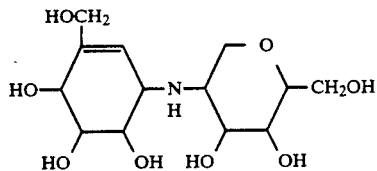

or a physiologically acceptable salt thereof.

2. A process for the preparation of a compound of the formula I as claimed in claim 1, which comprises cultivating the microorganism Streptomyces albus ATCC 21838 or one of its mutants or variants, isolating the compound of the formula I from the culture filtrate and/or the mycelium, and purifying it.

3. The process as claimed in claim 2, wherein the cultivation is carried out under submerse, aerobic conditions.

4. A pharmaceutical preparation, which contains a pharmaceutically effective amount of a compound of the formula I as claimed in claim 1 together with pharmacologically tolerated excipients.

5. A method for the inhibition of glycosidase which comprises administering to a human or homothermal animal in need of said inhibition an effective amount for said inhibition of a compound of the formula I as claimed in claim 1.

6. A method for the therapy of metabolic diseases which comprises administering to a human or homothermal animal in need of said therapy an effective amount of a compound of the formula I as claimed in claim 1.

7. A plant protection agent, containing an effective amount of a compound of the formula I as claimed in claim 1 together with an acceptable formulation auxiliary.

8. A method for the preparation of a plant protection agent which comprises incorporating as the active ingredient in said agent an effective amount of a compound of the formula I as claimed in claim 1.

9. A method of protecting plants from insects and/or harmful fungi, which comprises treating the plants with a compound as claimed in claim 1.

* * * * *